(12) United States Patent
Aviram et al.

(10) Patent No.: US 6,977,089 B1
(45) Date of Patent: Dec. 20, 2005

(54) METHODS OF USING POMEGRANATE EXTRACTS FOR CAUSING REGRESSION IN LESIONS DUE TO ARTERIOSCLEROSIS IN HUMANS

(75) Inventors: Michael Aviram, Kiriat-Haim (IL); Leslie Dornfeld, Los Angeles, CA (US)

(73) Assignee: Stewart and Lynda Resnick Revocable Trust, Los Angeles, CA (US)

( * ) Notice: Subject to any disclaimer, the term of this patent is extended or adjusted under 35 U.S.C. 154(b) by 0 days.

(21) Appl. No.: 10/701,918

(22) Filed: Nov. 4, 2003

Related U.S. Application Data

(63) Continuation of application No. 09/998,883, filed on Nov. 19, 2001, now Pat. No. 6,641,850, which is a continuation-in-part of application No. 09/294,307, filed on Apr. 19, 1999, now Pat. No. 6,387,418.

(60) Provisional application No. 60/318,160, filed on Sep. 6, 2001.

(51) Int. Cl.$^7$ ............................................ A61K 35/78
(52) U.S. Cl. .................... 424/769; 424/776; 424/777; 514/824
(58) Field of Search .............................. 424/769, 777, 424/776; 514/824

(56) References Cited

U.S. PATENT DOCUMENTS

| 6,387,418 B1 * | 5/2002 | Aviram et al. ............... 424/744 |
| 6,641,850 B1 * | 11/2003 | Aviram et al. ............... 424/769 |
| 2002/0012710 A1 * | 1/2002 | Lansky ....................... 424/725 |

FOREIGN PATENT DOCUMENTS

| JP | 404124140 A | * | 4/1992 |
| JP | 410298094 A | * | 11/1998 |

OTHER PUBLICATIONS

International Product Alert Bulletin. Rubyan Persia Pomegranate Concentrate Extract. Dec. 15, 1997. PROMT Abstract.*

\* cited by examiner

Primary Examiner—Christopher R. Tate
(74) Attorney, Agent, or Firm—Dalina Law Group P.C.

(57) ABSTRACT

Methods of using pomegranate extracts of the present invention for treating patients with atherosclerosis, or increased intima-media thickness of an artery, are provided. The methods comprise the step of administering to the patient a composition comprising a therapeutically effective amount of an extract from pomegranate. The methods of the present invention may also be used to decrease the incidence of stroke or heart attack in a patient.

18 Claims, 9 Drawing Sheets

METHODS OF USING POMEGRANATE EXTRACTS FOR CAUSING REGRESSION IN LESIONS DUE TO ARTERIOSCLEROSIS IN HUMANS

RELATED APPLICATION

This is a continuation of application Ser. No. 09/998,883, filed Nov. 19, 2001 now U.S. Pat. No. 6,641,850, which is a continuation-in-part of application Ser. No. 09/294,307, filed on Apr. 19, 1999 now U.S. Pat. No. 6,387,418, the contents of which are hereby incorporated herein by reference. This application also claims priority to the U.S. provisional Application Ser. No. 60/318,160, filed on Sep. 6, 2001, under 35 U.S.C. 119(e), the content of which is hereby incorporated herein by reference.

BACKGROUND OF THE INVENTION

1. Area of the Art

The invention relates generally to pomegranate extracts and methods of using thereof, and specifically to methods of using pomegranate extracts for causing regression in lesions due to arteriosclerosis in humans.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Oxidative stress, a major contributor to cardiovascular diseases (1), is associated with lipid peroxidation in arterial macrophages and in lipoproteins (1–3). Oxidized low-density lipoprotein (Ox-LDL) was shown to be atherogenic (2–4), thus, interventions to inhibit LDL oxidation by dietary antioxidants (4, 5) is of major importance to attenuate atherosclerosis. It was recently shown that vitamin E supplementation to patients with carotid artery stenosis inhibited LDL accumulation in arterial macrophages (6). Protection of lipids from oxidation can be also achieved by serum paraoxonase (PON1), an HDL-associated esterase that can hydrolyze and reduce specific lipid peroxides in arterial cells and lipoproteins in coronary and carotid lesions (7–10).

The pomegranate was recently chosen as the logo for the Millennium Festival of Medicine, mainly because of its medicinal properties as described by all major religions and by folk medicine (11). Pomegranate juice (PJ) possesses impressive antioxidative properties due to its high flavonoids content, mainly the water soluble tannins and proanthocyanins (12). We have recently shown the antioxidative and antiatherogenic characteristics of PJ consumption in atherosclerotic apolipoprotein E deficient ($E^o$) mice (13). In healthy humans, PJ consumption also demonstrated potent antioxidative capabilities against lipoprotein oxidation, and also increased PON1 activity and improved serum total antioxidant status (13).

A need exists, however, to study whether the above beneficial effects of PJ can be manifested in patients with atherosclerosis such as carotid artery stenosis.

SUMMARY OF THE INVENTION

The present invention is based on the unexpected discovery that pomegranate juice consumption by a patient with atherosclerosis may cause regression of the size of atherosclerotic lesions. Prior to the present invention, it has been observed that pomegranate juice consumption by $E^o$ mice may slow down the progression of arteriosclerosis, and reduce the expected increase in the size of atherosclerotic lesions. It is the discovery of the present invention that pomegranate juice consumption by a patient with atherosclerosis, however, not only can slow down the progression of arteriosclerosis, but also can reduce the size of atherosclerotic lesions that are already developed, and therefore cause regression of the lesion size.

Accordingly, one aspect of the present invention provides a method for treating a patient with arteriosclerosis. The method comprises the step of administering to the patient a composition comprising a therapeutically effective amount of an extract from pomegranate fruit. According to embodiments of the present invention, the arteriosclerosis may be carotid artery arteriosclerosis or coronary artery arteriosclerosis. The extract of pomegranate may be a juice extract of pomegranate, an extract from inner or outer peel of pomegranate, or the mixture thereof.

Another aspect of the present invention provides a method of treating a patient with an increased intima-media thickness of an artery. The method comprises the step of administering to the patient a composition comprising an amount of an extract from pomegranate which is therapeutically effective to reduce the intima-media thickness of the artery. According to embodiments of the present invention, the intima-media thickness of the artery is due to arteriosclerosis, such as, but not limited to, coronary artery arteriosclerosis and carotid artery stenosis, diabetes, high blood pressure, and peripheral vascular disease.

A further aspect of the present invention provides a method of decreasing the incidence of stroke and heart attack in a patient. The method comprises the step of administering to the patient a composition comprising a therapeutically effective amount of an extract from pomegranate. According to the embodiments of the present invention, the stroke or the heart attack is associated with artery arteriosclerotic diseases, including but not limited to, coronary artery arteriosclerosis and carotid artery stenosis, diabetes, high blood pressure, and peripheral vascular disease.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which:

FIG. 8A shows the effect of PJ consumption on the cholesterol level of the plaque. FIG. 8B shows the effect of PJ consumption on lipid peroxides of the plaque. FIG. 8C shows the effect of PJ consumption on carotid GSH of the plaque. FIG. 8D shows the effect of PJ consumption on LDL oxidation of the lesion.

DETAILED DESCRIPTION OF THE INVENTION

Figure 1:
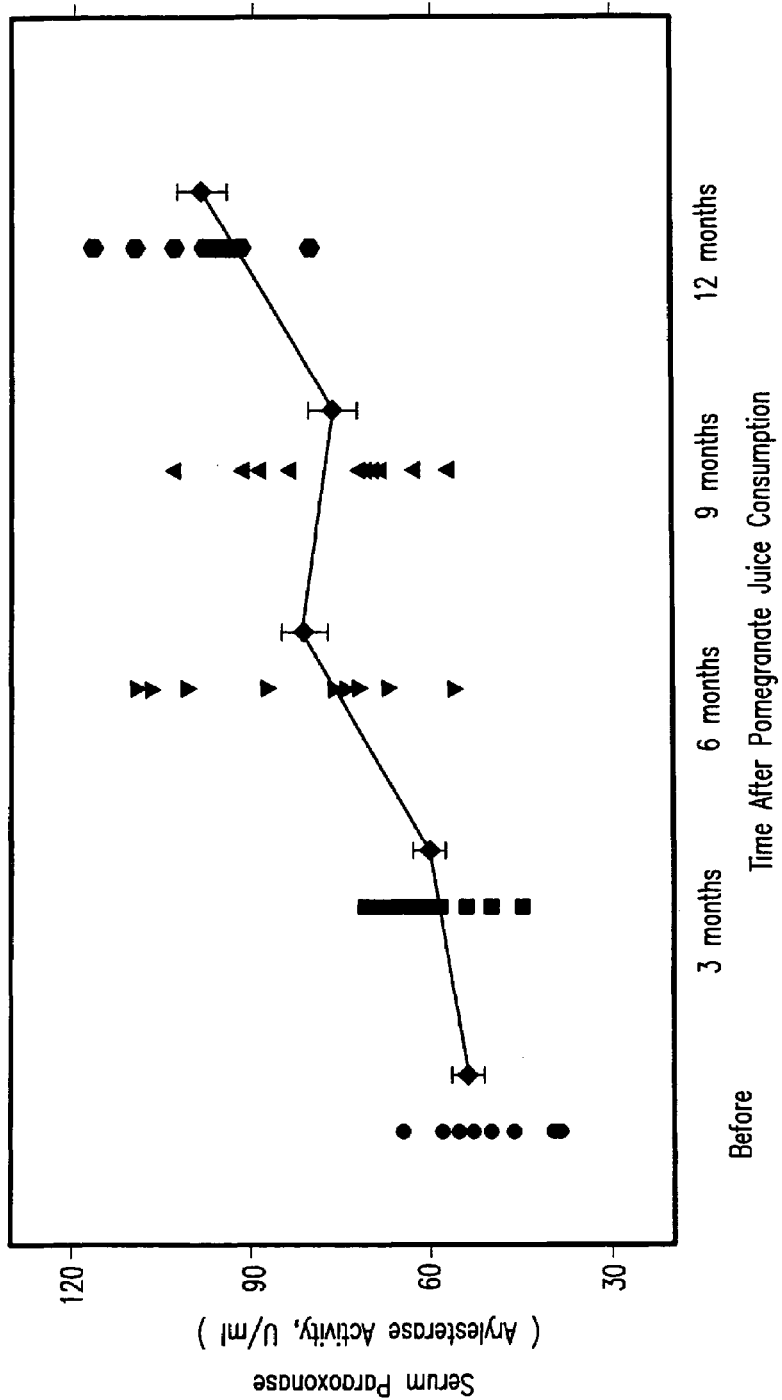
FIG. 1 shows the effect of pomegranate juice consumption by patients with carotid artery stenosis on serum paraoxonase.

One aspect of the present invention provides a method for treating a patient with arteriosclerosis. The method comprises the step of administering to the patient a composition comprising a therapeutically effective amount of an extract from pomegranate.

For the purpose of the present invention, an extract from pomegranate may be an extract from the whole pomegranate fruit or from any constituents of pomegranate fruit. Examples of constituents of pomegranate fruit that may be used to make the extract of the present invention include, but are not limited to, juice, seed, and the inner and outer peel of pomegranate fruit. In one embodiment of the present invention, the extract is the juice extract of whole pomegranate fruit. In another embodiment of the present invention, the extract is from the inner or outer peel of pomegranate fruit. In a further embodiment of the present invention, the extract may be a mixture of two or more extracts of the whole pomegranate or any constituents of pomegranate.

Methods of making the juice extract of whole pomegranate fruits are commonly known in the art, and need not be repeated here. In general, any methods that may produce pomegranate juice that naturally occurs in pomegranate may be used. For the purpose of the present invention, the juice may be concentrated or diluted from its natural concentration. The juice may also be mixed with extracts of other constituents of pomegranate.

Extracts from the constituents of pomegranate, i.e., seeds or the inner or outer peel, may be made by methods commonly known in the art. For example, the seeds or the inner or outer peel of pomegranate may be diluted in water and the extract may be made by crushing, squeezing, or extensive vortexing. The insoluble materials of the extract may be separated from the soluble supernatant of the extract. Preferably, the supernatant of the extract is used for the purpose of the present invention, although any oily, lipidic fraction of the extract may also be used. The extract from constituents of pomegranate may be concentrated or diluted, or mixed with each other or with pomegranate juice extract.

In accordance with one embodiment of the present invention, the extract of the present invention may be prepared by a process including the steps of: (a) crushing and squeezing the whole fruits of the pomegranate, including the inner and outer peels and the seeds, to yield a juice component and an insoluble by-product component, and (b) separating the juice component from the insoluble by-product component. The juice component may be used as a juice extract of the present invention. The insoluble by-product component may be resuspended in an aqueous medium, such as, but not limited to, water or alcohol, and be further crushed, squeezed, and mixed to yield a soluble portion and an insoluble portion. Then the soluble portion may be separated from the insoluble portion to produce the extract of the constituents of the present invention. Alternatively, the soluble portion may be combined with the juice extract to produce the extract of the present invention.

In one embodiment of the present invention, the whole fruit of the pomegranate may be enzymatically treated to improve extraction and filtration. For example, pectinase may be used to treat the whole fruit to prevent the formation of pectin gels. Other enzymes known in the art may also be used as long as they can improve extraction and filtration of the extract of the present invention.

The extract of pomegranate of the present invention may be in a liquid or solid form. In accordance with one embodiment of the present invention, a solid form of the extract may be made by lyophilizing the liquid extract of the present invention. Alternatively, the constituents of the pomegranate, such as seeds, inner or outer peels, or any insoluble portion discussed above, may be processed directly to form the solid form of the extract of the present invention. For example, the constituents of the pomegranate may be dried, and processed into powder or pill forms to be used directly as the solid form of the extract of the present invention.

Compositions of the present invention may be a variety of kinds, including, but not limited to, nutritional supplements, pharmaceutical preparations, vitamin supplements, food additives, or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions of the present invention may include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form. As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

In one embodiment of the present invention, a composition contains the extract of pomegranate in a dosage unit in an amount that contains at least 30 to 3000 $\mu$mols per dosage unit of polyphenols. For the purpose of the present invention, polyphenols are those naturally present in the extract of pomegranate. It should be appreciated that polyphenols are used herein as a measurement marker for the amount of extract that needs to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

The term "dosage unit" as used herein refers to physically discrete units suitable as unitary dosages for animals, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutical use in animals.

The term "therapeutically effective amount" as used herein means that the amount of the extract of the present invention contained in the composition administered is of sufficient quantity to achieve the intended purpose, such as, in this case, to cause regression of arteriosclerosis in the patient. For the purpose of the present invention, regression of arteriosclerosis may be measured by the decrease in the size of lesions caused by arteriosclerosis. Methods of measuring the lesion size is well known in the art, and need not be repeated herein. For example, ultrasound and angiography methods may be used to measure the lesion size. In accordance with one embodiment of the present invention, the regression is determined by measuring the intima-media thickness of an artery, such as, but not limited to, carotid artery or coronary artery.

Accordingly, by determining the regression of arteriosclerosis in a patient, one skilled in the art can readily determine whether the amount of the extract of the present invention is therapeutically effective in view of the disclosure of the present invention without undue experimentation. In one embodiment, the therapeutically effective amount of the extract of the present invention contains at least 30 to 3000 $\mu$mols of polyphenols naturally occurring in a pomegranate fruit. Again, it should be appreciated that the polyphenols are used herein as a measurement marker for the concentration of the extract of the present invention. In another embodiment, the composition contains one glass of juice extract of the present invention.

The method of the present invention may be used to treat patients with arteriosclerosis, particularly patients with carotid or coronary artery arteriosclerotic diseases. In addition, the methods of the present invention may be used to treat patients with an increased intima-media thickness of an artery, particularly to treat patients with an increased intima-media thickness of carotid artery or coronary artery caused by carotid artery arteriosclerosis or coronary artery arteriosclerosis, respectively. Furthermore, since artery arteriosclerosis is closely associated with the incidence of stroke and heart attack, the methods of the present invention may also be used to decrease the incidence of stroke and heart attack in a patient, particularly those associated with carotid or coronary artery arteriosclerotic disease.

Accordingly, another aspect of the present invention provides a method of treating a patient with an increased intima-media thickness of an artery. The method comprises the step of administering to the patient a composition comprising an amount of an extract from pomegranate which is therapeutically effective to reduce the intima-media thickness of the artery. The term "therapeutically effective" as used herein means that the amount of the extract of the present invention contained in the composition administered is of sufficient quantity to reduce the intima-media thickness of the artery. According to one embodiment of the present invention, the intima-media thickness of the artery may be due to arteriosclerosis, such as, but not limited to, coronary artery arteriosclerosis and carotid artery stenosis, diabetes, high blood pressure, and peripheral vascular disease.

A further aspect of the present invention provides a method of decreasing the incidence of stroke or heart attack in a patient. The method comprises the step of administering to the patient a composition comprising a therapeutically effective amount of an extract from pomegranate to decrease the incidence of stroke or heart attack in a patient. As used herein, the term "therapeutically effective" means that the amount of the extract of the present invention contained in the composition administered is of sufficient quantity to decrease the incidence of stroke or heart attack in a patient. The decrease in the size of the plaque or increase in the stability of the plaque at the lesion of a patient may decrease the incidence of stroke or heart attack. According to one embodiment of the present invention, the stroke or the heart attack may be associated with arteriosclerotic diseases, including, but not limited to, carotid or coronary artery arteriosclerotic disease, and peripheral vascular disease.

The following examples are intended to illustrate, but not to limit, the scope of the invention. Indeed, those of ordinary skill in the art can readily envision and produce further embodiments, based on the teachings herein, without undue experimentation.

EXAMPLES

Methods

Pomegranate Processing

Pomegranates were picked by hand, washed, chilled to 32° F., and stored in tanks. Then the fruit was crushed, squeezed, and enzymatically treated with pectinase to yield the pomegranate juice and the by-products, which include the inner and outer peels and the seeds. Pectinase hydrolyzes alpha-1.4 galacturonide bonds in pectin and, thus, it improves extraction and filtration, and prevents formation of pectin gels. The juice was filtered, pasteurized, concentrated, and stored at −18° C.

Alternatively, pomegranates were picked by hand, washed, and stored in tanks. Then, the fruits were crushed and squeezed. The juice was filtered, pasteurized, concentrated, and stored at −18° C. Each day during the study period, the concentrated PJ was diluted 1:5 (v:v) with water in order to obtain a single strength PJ.

Peels and Seeds Extracts

One gram of inner or outer peels/seeds was diluted in 5 ml of water followed by crushing, squeezing, and extensive vortexing. Then, the extract was centrifuged to remove any water insoluble materials and the supernatant was used alone or mixed with the juice extract for use in the methods of the present invention.

In the seeds extraction, an upper oily, lipidic fraction appeared which was not used in the study of aqueous extracts, but may also contain some active compounds. Therefore, the oily, lipidic fraction may also be used as an extract of the present invention.

Polyphenols Determination

Total polyphenols concentration in pomegranate juice was determined spectrophotometrically with the phosphomolybdic phosphotungstic acid reagents (26).

LDL Isolation

LDL is isolated from blood samples by discontinuous density gradient ultracentrifugation and is then dialyzed against saline with EDTA (1 mmol/L) (14). Before the oxidation study, LDL is diluted in phosphate buffered saline (PBS) to 100 mg protein/L and dialyzed overnight against PBS at 4° C. to remove the EDTA. LDL protein concentration is determined with the Folin phenol reagent (15).

LDL Oxidation

Oxidation of LDL is carried out in a shaking water bath at 37° C. under air, in plastic tubes, 1 cm in diameter. For metal ion-dependent oxidation, LDL is incubated for 4 hours at 37° C. with freshly prepared $CuSO_4$ (5 $\mu$mol/L).

B-Mode Ultrasonography

Common carotid artery IMT from B-mode ultrasound is a widely used measure of early atherosclerosis (36–38). After a careful axial scan, longitudinal B-mode images of common carotid artery wall boundaries were obtained with a high resolution (7 $MH_z$ linear transducer, Acuson 128×P, Acuson Co, Mountain View, Calif.). Maximum IMT was measured at the far wall of the distal common carotid arteries, about one centimeter from the carotid bifurcation. Atherosclerotic plaques at the common carotid arteries and the carotid bulb, as well as the proximal and distal internal carotid arteries were imaged and the length and width of the plaque were assessed. On duplex examination of the internal carotid arteries, flow velocities were calculated at the stenotic sites, and expressed by peak systolic velocity (PSV) and EDV. The ultrasound outcome analyses were the change over time in the maximal IMT among the same preselected carotid artery segment, and the change in the plaque dimensions and in blood flow velocities. Patients had up to five B-mode and duplex examinations of the common and internal carotid arteries on both sides. There was one ultrasound examination at baseline, one every 3 months and one at the final clinical visit after 12 months of PJ consumption. All ultrasound studies were done by the same physician assuring reproducibility of the site of IMT and plaques measurements, as well as site and interrogation angles on the duplex follow-up examinations. The sonologist was aware of the results of measurements on previous examinations. In order to avoid the potential introduction of scanner-dependent variabilities, the same ultrasound system was used for individual patients on follow-up examinations.

For metal ions-dependent oxidation, LDL (100 $\mu$g of protein/ml) was incubated for 2 hours at 37° C. with freshly prepared $CuSO_4$ (5 $\mu$M). LDL oxidation was terminated by refrigeration at 4° C., and the addition of 0.1 mM $Na_2$ EDTA and 25 $\mu$M BHT to the $CuSO_4$ system. The formation of conjugated dienes was continuously monitored by measuring the increase in absorbency at 234 nm (60). The lag time required for initiation of lipoprotein oxidation was calculated from the oxidation curve. The amount of LDL-associated lipid peroxides was measured by the method of El-Saadani et al. (39).

For metal ions-independent oxidation, LDL is incubated for 2 hours at 37° C. with 5 mM AAPH. $Na_2$ EDTA (0.1 mM) is added to the incubation medium in order to chelate adventitious metal ions that could otherwise contribute to the radical initiator-induced oxidation. LDL oxidation is terminated by refrigeration at 4° C. LDL oxidation is determined by measuring the amount of thiobarbituric acid reactive substances (TBARS), lipid peroxides formation, and by continuous monitoring of the formation of conjugated dienes by measuring the increase in absorbance at 234 nm.

For macrophage-mediated oxidation, J-774 A.1 macrophages ($2 \times 10^6$ cells/35 mm dish, obtained from the American Tissue Culture Collection, Rockville, Md.), is incubated with LDL (100 $\mu$g of protein/ml) for 18 hours at 37° C. in medium Ham's F-10, in the presence of 2 $\mu$M $CuSO_4$. The extent of LDL oxidation is measured directly in the medium by the TBARS assay. LDL incubated under similar conditions in the absence of cells (cell-free) serves as a control. Cell-mediated oxidation of LDL is calculated by subtracting the cell-free value from the value obtained in the presence of cells. LDL oxidation is determined by measuring the amount of thiobarbituric acid reactive substances (TBARS) (16).

The formation of conjugated dienes is continuously monitored by measuring the increase in absorbance at 234 nm (17). Incubations are carried out in the spectrophotometer cuvette at 37° C. in a thermostatic six-cell holder in a spectrophotometer (Ultrospec 3000, Pharmacia, Biotech). The reference cell contains 5 $\mu$mol/L $CuSO_4$ in PBS, or 1 mmol/L of AAPH, together with 0.1 mM EDTA in PBS, for metal ion dependent or metal ion-independent oxidation, respectively. The increase in absorbance during LDL oxidation is recorded over time every ten minutes.

The LDL-associated lipid peroxide formation is determined with a commercially available kit (cholesterol color reagent, CHOD iodide method, Diagnostica Merck, Darmstadt, Germany) (18). This assay is based on the oxidative activity of lipid peroxides that convert iodide to iodine and is measured spectrophotometrically. The assay is performed with 100 $\mu$l of lipoprotein solution (100 mg protein/ml) which is mixed on a vortex with 1 ml color reagent. The sample is allowed to stand for 30 minutes in the dark, followed by a determination at 365 nm against a blank solution.

LDL Aggregation

LDL (100 $\mu$g of protein/mL) is mixed by vortex at a fixed strength, and the absorbance at 680 nm is monitored every 10 seconds against a blank solution (19). LDL aggregation is also induced by its subjection to the action of sphyngomyelinase (SMase) or phospholipase C (PLase C) (61).

LDL Retention

LDL (200 $\mu$g of lipoprotein protein/mL) is incubated with chondroitin sulfate (CS, 100 $\mu$g/mL) for 30 minutes at room temperature. The lipoprotein is precipitated with a commercial kit for HDL cholesterol reagent (phosphotungstic acid/ $MgCl_2$, Sigma Co., St. Louis, Mo.) that precipitates all the LDL present in the samples, followed by a 10-minute centrifugation at 2000×g (20). After discarding the supernatant, the LDL in the precipitate is dissolved in 0.1 N NaOH, and analyzed for its glycosaminoglycans (GAGs) content using the 1,9-dimethylmethylene blue (DMMB)

spectrophotometric assay for sulfated glycosaminoglycans (21). The absorbency at 525 nm is then immediately measured.

Paraoxonase Activity

Paraoxonase is determined as its arylesterase activity (22). Arylestrase activity is measured using phenylacetate as the substrate. The initial rates of hydrolysis are determined spectrophotometrically at 270 nm. The assay mixture includes 1.0 mM phenylactate and 0.9 mM $CaCl_2$ in 20 mM Tris HCl, pH 8.0. Non-enzymatic hydrolysis of phenylacetate is subtracted from the total rate of hydrolysis. The $E_{270}$ for the reaction is 1,310 $M^{-1}$ $cm^{-1}$. One unit of arylesterase activity is equal to 1 μmol of phenylacetate hydrolyzed/min/ml. A purified enzyme has nearly 2000 units of arylesterase activity per mg protein.

Human Studies

Nineteen patients, 5 females and 14 males, ages 65–75 years, with asymptomatic severe carotid artery stenosis (CAS, defined as 71–90% stenosis of one of the carotid arteries), were included in the study. These patients had an abnormal echo doppler of the carotids, which was performed following a finding of carotid murmur in physiological examination, or complaints of headache or dizziness. Their dietary habits and life style did not change during the study. The patients were under several hypotensive drugs, and continued this therapy along the study. Nine patients that did not consume PJ served as the control group. In these patients, the echo doppler of the carotid arteries was performed at the beginning of the study and after one year. Ten patients consumed 1 glass of PJ (1:5, v:v dilution of concentrated PJ which contained 1.5 mmoles total polyphenols equivalents) in the evening for a period of up to 12 months. Blood analyses and echo doppler of the carotid arteries were performed at the beginning of the study and at 3, 6, 9, and 12 months after starting PJ consumption. Blood samples were also taken 1 month after the termination of PJ consumption. Blood pressure was monitored in the morning in a sitting position. The study was approved by the Helsinki Committee of the Rambam Medical Center, Israel Ministry of Health.

Echo Doppler Evaluation

All patients had a complete echo doppler evaluation of the carotid arteries including intimal-medial thickness. The ultrasonographic images of both carotid arteries were analyzed before pomegranate juice consumption, and after 3, 6, 9, and 12 months of juice consumption. The examinations were performed by B-mode high resolution ultrasonography with a 7–10 MHz transducer. The intima-media complex thickness was measured at the common carotid artery 2 cm proximal to the bifurcation (23, 24). Each atherosclerotic plaque, both in the common and in the internal carotid artery, was imaged for size and configuration of the plaque (soft, calcified, ulcerated). Progression/regression of stabilization of carotid arteriosclerosis was determined for each plaque and intima-media thickness measurement. A pulsed echo doppler examination combined with a B-mode ultrasound (Duplex) was performed at stenotic artery segments. Peak systolic and diastolic velocities were measured and internal carotid/common carotid ratios were then calculated.

Blood Analysis

1. Biochemical tests in serum, which includes the measurement of serum glucose, createnine, urea, billirubin, creatine kinase, and aspartate amino transferase by conventional means known in the art.

2. Liver function tests by known methods.

3. Kidney function tests by known methods.

4. Plasma lipids profile, including total cholesterol, LDL-, VLDL-, and HDL-cholesterol and total triglycerides phospholipids, apolipoproteins A–I and apolipoprotein B-100 concentrations. Known conventional means are used to conduct the measurements.

5. Plasma susceptibility to oxidation induced by a free radical generating system, AAPH (2,2'-azobis 2-amidino-propane hydrochloride), which is an aqueous soluble azo compound that thermally decomposes to produce peroxyl radicals at a constant rate. Plasma susceptibility to oxidation is analyzed following incubation of 1 ml of plasma for 2 hours at 37° C. with 100 mM AAPH. The formation of thiobarbituric acid reactive substances (TBARS) and of lipid peroxides is measured in comparison to plasma that is incubated under similar conditions, but without AAPH.

6. Total antioxidant status (TAS) in plasma is evaluated by methods known in the art. Total antioxidant status was measured in serum with a commercially available kit (catalog no. NX 2332; Randox Laboratories, Antrim, United Kingdom, 19).

7. Serum anti Ox-LDL antibodies: The amount of serum anti Ox-LDL antibodies was measured in serum samples collected from the patients before treatment and after 3 or 6 months of PJ consumption, by using the immunoelisa anti-Ox-LDL test (Immco Diagnostics, Inc. Buffalo, N.Y., USA, Cat. No 1158). Results are expressed as Enzyme Units per milliliter (EU/ml).

8. Total polyphenols in plasma is measured as described above.

9. Paraoxonase (an HDL-associated esterase that protects from lipid peroxidation) activity in serum. Paraoxonase is determined as its arylesterase activity described above.

10. Separation of VLDL, LDL and of HDL from plasma by ultracentrifugation and determination of their lipid content.

Plasma samples drawn from the patients before and after 1, 3, 6, 9, and 12 months of PJ consumption were stored at −20° C. until all samples were collected. Plasma lipoproteins (LDL, VLDL, HDL) were isolated by sequential density ultra-centrifugation (19). The LDL was washed at d=1.063 g/mL, and dialyzed against 150 mmol/L NaCl and 1 mmol/L $Na_2$ EDTA (pH 7.4) at 4° C. The LDL fractions were then sterilized by filtration (0.45 μm), kept under nitrogen in the dark at 4° C., and used within 2 weeks. The lipoprotein protein concentration was determined by the Lowry assay (59). Prior to oxidation, LDL was dialyzed against EDTA-free, phosphate-buffered saline (PBS) solution at pH 7.4, and at 4° C. All lipoproteins were analyzed for their content of protein, total and unesterified cholesterol, triglycerides, phospholipids, vitamin E, and carotenoids.

11. Basal Oxidative State of LDL including measurement of cholesteryl ester and cholesteryl ester hydroperoxides by HPLC, as discussed above.

12. LDL Susceptibility to Oxidation. LDL is dialyzed for 24 hours against phosphate buffered saline (PBS) before oxidation to remove the EDTA. Oxidation of LDL is carried out in a shaking water bath at 37° C. under air. LDL is subjected to oxidation by copper ions, by AAPH, as well as by macrophages in cell culture.

13. Serum Angiotensin II Converting Enzyme (ACE) Activity. ACE activity is analyzed spectrophotometrically in order to evaluate possible effects of pomegranate juice on atherosclerosis via this pathway.

14. Carotid Lesion: Complete atherosclerotic plaques, including the common internal and external carotid parts of the plaque, were removed from seven patients that did not consume PJ and from two patients that consumed PJ for 3 or 12 months. Lesions were washed in saline, dried, and their weight measured. The lesions were cut into small pieces and rinsed in PBS, followed by their sonication in an ultrasonic processor (3×20 seconds at 80 W). The lesion's cholesterol content was measured in the homogenate samples by an enzymatic, colorimetric assay using a commercial kit (Sigma Co. Ltd). Lesion's lipid peroxides content was also measured (41). Reduced glutathione (GSH) content was measured by the (DTNB)-GSSG reductase recycling assay (42).

15. Statistics: The ANOVA test was performed for all statistical analyses. Results are given as the mean±SEM. Assays in each sample were performed in triplicate. All comparisons are shown for data after PJ consumption vs. the results obtained before treatment.

Results

The results of the echo doppler evaluation of the seven male and three female patients with asymptomatic severe carotid stenosis are summarized in Table 1. Table 1 shows the effect of pomegranate juice consumption on intima-media thickness (IMT) of the patients with carotid artery stenosis. The results indicate that pomegranate juice consumption by the patients can reduce the size of lesions already formed. The intima-media thickness of the carotid artery showed regression of the size of the lesions.

TABLE 1

The Effect of Pomegranate Juice Consumption on Intima-Media Thickness (IMT) in Patients with Carotid Artery Stenosis

| Patient (#) | 0 | 3 Months | 6 Months | 9 Months | 12 Months |
|---|---|---|---|---|---|
| A. Right | | | | | |
| 1 | 1.7 | 1.3 | 1.2 | 1.1 | 0.8 |
| 2 | 1.3 | 1.3 | 1.2 | 1.0 | 0.8 |
| 3 | 1.3 | 1.3 | 1.2 | 0.7 | 0.6 |
| 4 | 2.7 | 2.7 | 2.2 | 2.0 | 1.4 |
| 5 | 2.8 | 2.8 | 2.7 | 2.1 | 1.2 |
| 6 | 1.8 | 1.8 | 1.3 | 1.3 | 0.9 |
| 7 | 1.9 | 1.9 | 1.7 | 1.1 | 0.9 |
| 8 | 3.8 | 3.8 | 2.2 | 1.9 | 1.7 |
| 9 | 1.8 | 1.7 | 1.5 | 1.0 | 0.8 |
| 10 | 1.9 | 1.9 | 1.6 | 1.5 | 1.2 |
| B. Left | | | | | |
| 1 | 1.1 | 1.1 | 1.0 | 0.8 | 0.6 |
| 2 | 1.0 | 1.0 | 0.9 | 0.8 | 0.6 |
| 3 | 1.3 | 1.2 | 0.9 | 0.7 | 0.6 |
| 4 | 2.3 | 2.3 | 2.0 | 1.4 | 1.1 |
| 5 | 2.3 | 2.3 | 1.7 | 1.2 | 0.7 |
| 6 | 2.3 | 2.2 | 1.3 | 1.1 | 0.8 |
| 7 | 2.5 | 2.2 | 2.1 | 1.9 | 1.2 |
| 8 | 3.7 | 2.4 | 1.9 | 1.6 | 1.0 |
| 9 | 2.8 | 2.6 | 2.4 | 2.3 | 1.8 |
| 10 | 2.8 | 2.6 | 2.5 | 2.3 | 1.8 |

The effect of pomegranate juice (PJ) consumption by patients with carotid artery stenosis on the lesion content of lipids, oxidized lipids, GSH and on the lesion-mediated oxidation of LDL is also measured, and the results are summarized in Table 2. Lesions were obtained from patients with carotid artery stenosis; seven of the patients did not consume PJ (control), and two of the patients consumed PJ for 3 or 12 months. The amount of cholesterol, triglyceride, lipid peroxides, and GSH (reduced glutathione) were measured in the lesions homogenates as described above. Lesions (0.3 g) were incubated with LDL

TABLE 2

The effect of pomegrante juice (PJ) consumption by patients with carotid artery stenosis on lesion content of lipids, oxidized lipids, GSH and on lesion-mediated oxidation of LDL.

| | Cholesterol (mg/mg lesion protein) | Triglyceride (mg/mg lesion protein) | Lipid Peroxides (nmol/mg lesion protein) | GSH (nmol/mg lesion protein) | Lesion-Mediated Oxidation of LDL (nmol peroxides/ mg LDL protein) |
|---|---|---|---|---|---|
| Control Lesions (n = 7) | 0.59 ± 0.14 | 0.33 ± 0.07 | 219 ± 17 | 0.26 ± 0.04 | 318 ± 24 |
| Lesion after 3 months of PJ consumption (n = 1) | 0.23 ± 0.06 | 0.20 ± 0.03 | 85 ± 5 | 0.63 ± 0.05 | 181 ± 11 |
| Lesion after 12 months of PJ consumption (n = 1) | 0.45 ± 0.08 | 0.09 ± 0.01 | 123 ± 8 | 0.67 ± 0.02 | 216 ± 15 |

(100 μg of protein per ml) in PBS for 20 hours at 37° C. LDL was also incubated under the same conditions without lesions. The extent of LDL oxidation was measured by the lipid peroxide assay. Lesion-mediated oxidation of LDL was calculated by subtracting the values obtained in control LDL from those obtained upon incubation of LDL with the lesions. Results summarized in Table 2 indicate that after pomegranate juice consumption, there was a decrease in total cholesterol, triglycerides, and lipid peroxides. LDL oxidation was also diminished. However, there was an increase in GSH. The analysis indicates that there were beneficial quantitative and qualitative changes in carotid artery lesions. In order to analyze the effect of PJ consumption on the patients' serum oxidative state, we measured the serum concentration of antibodies against Ox-LDL. A significant ($p<0.01$) reduction in the concentration of antibodies against Ox-LDL by 24% and 19% was observed after 1 and 3 months of PJ consumption, respectively, (from 2070±61 EU/ml before treatment to 1563±69 and 1670±52 EU/ml after 1 and 3 months of PJ consumption, respectively). Total antioxidant status (TAS) in serum was substantially (2.3 fold) increased from 0.95±0.12 nmol/L at baseline, up to 2.20±0.25 nmol/L after 12 months of PJ consumption. These results indicate that PJ administration to the patients substantially reduced their serum oxidative stress, and could thus inhibit plasma lipid peroxidation. The susceptibility of the patients' plasma to AAPH-induced oxidation was reduced after 12 months of PJ consumption by 62% (from 209±18 at baseline to 79±6 nmol of peroxides 1 ml after 12 months of PJ consumption. We next isolated the patients' LDL and analyzed their basal oxidative state, as well as the susceptibility of their LDL to copper ion-induced oxidation (FIGS. 1, 3 and 4).

FIG. 1 shows the effect of pomegranate juice consumption by patients with carotid artery stenosis on serum paraoxonase. FIG. 1 demonstrates a significant (p<0.01) increase in serum paraoxonase, measured as arylesterase activity, by 11%, 42%, 49%, and 83% after 3, 6, 9 and 12 months of PJ consumption, respectively. The results indicate that pomegranate juice consumption can significantly increase serum arylesterase activity (a major activity of the enzyme paraoxonase).

Figure 2:
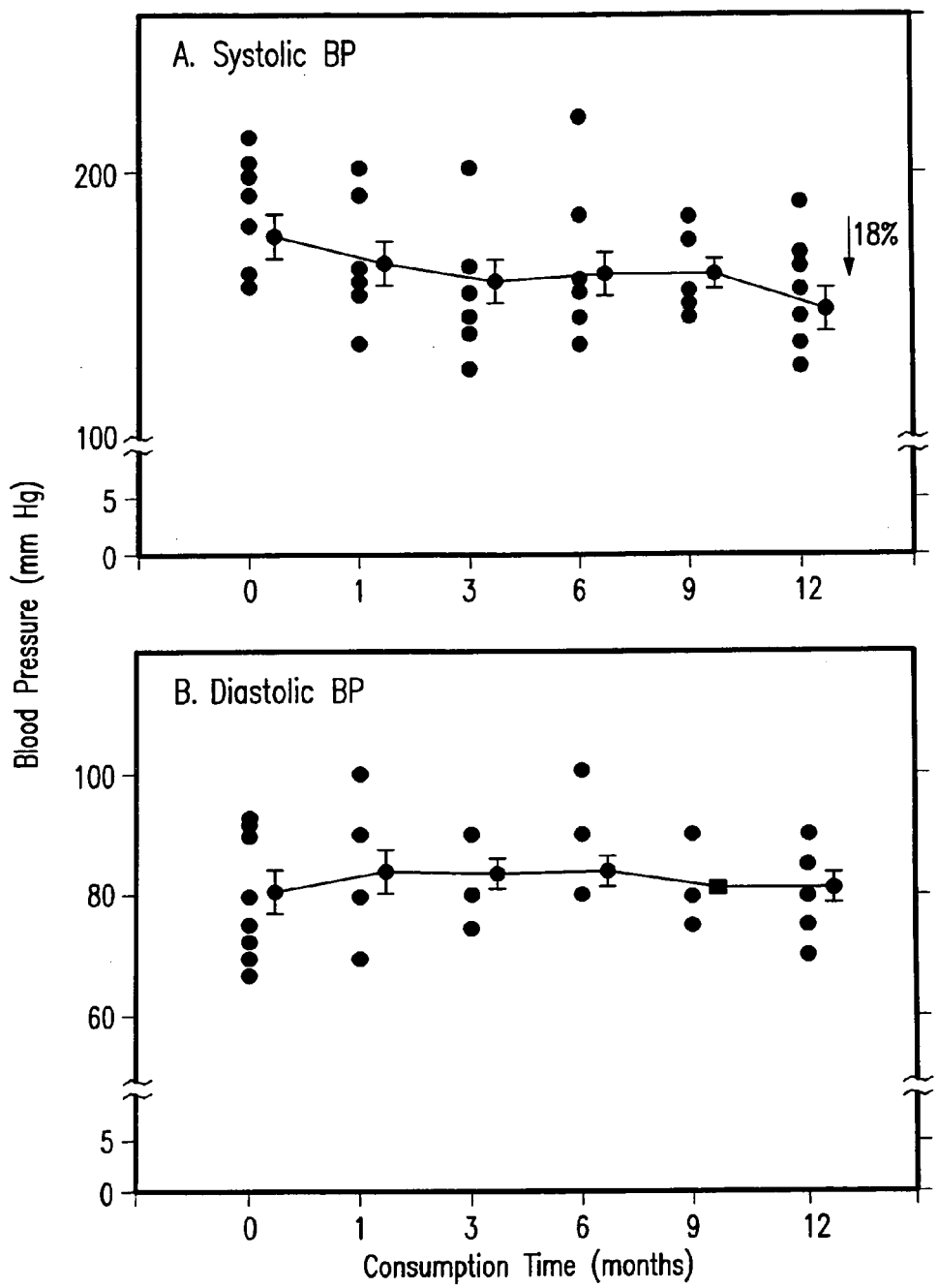
FIG. 2 shows the effect of pomegranate juice consumption by patients with carotid artery stenosis on their blood pressure.

FIG. 2 shows the effect of pomegranate juice consumption by patients with carotid artery stenosis on their blood pressure. After 12 months of PJ consumption, the patients' systolic blood pressures were significantly reduced by 18% compared to the values obtained before treatment (FIG. 2A). The results show that pomegranate juice consumption has no significant effect on diastolic blood pressure (FIG. 2B).

Figure 3:
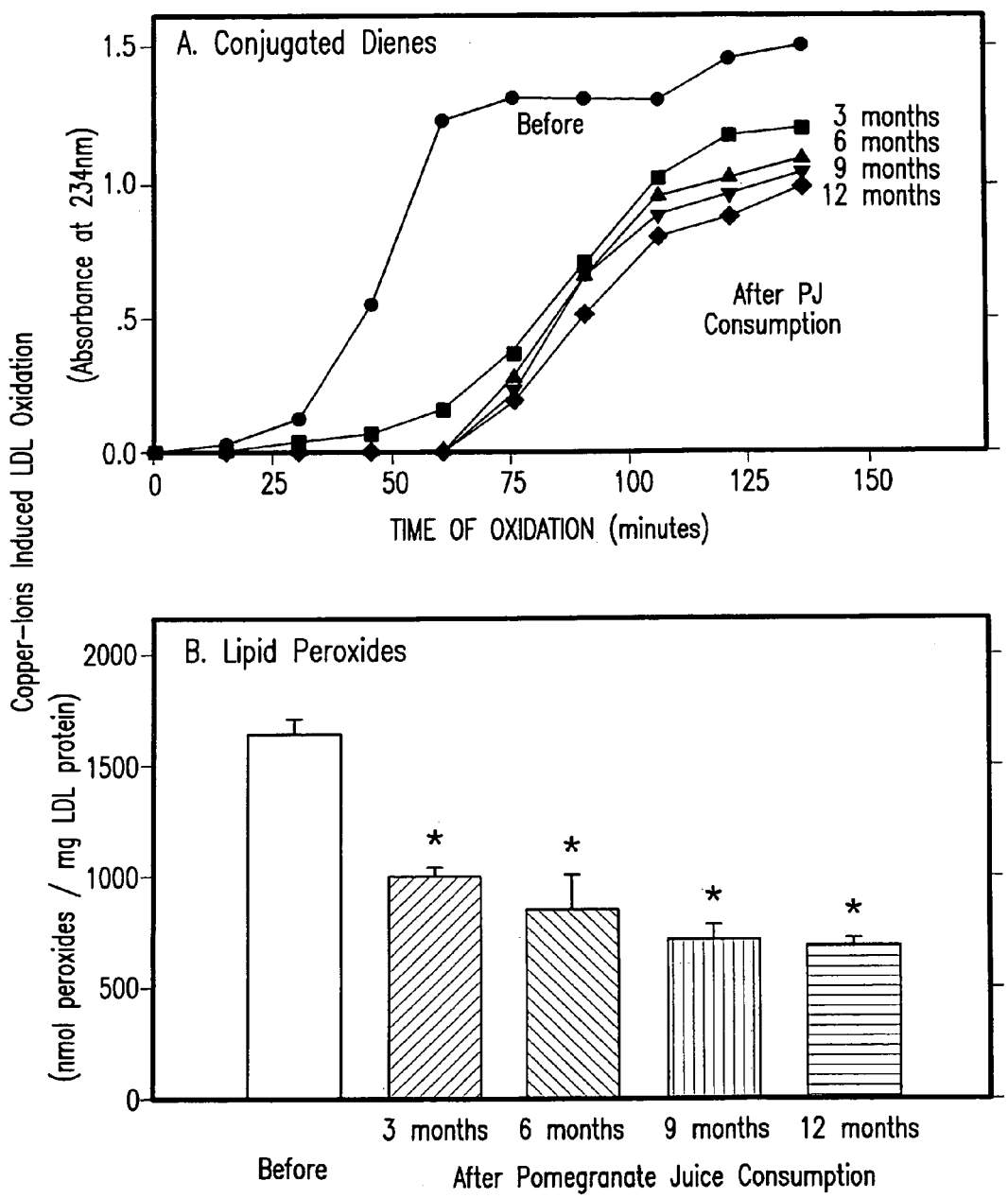
FIG. 3 shows the effect of pomegranate juice consumption by patients with carotid artery stenosis on copper ion-induced LDL oxidation.
Figure 4:
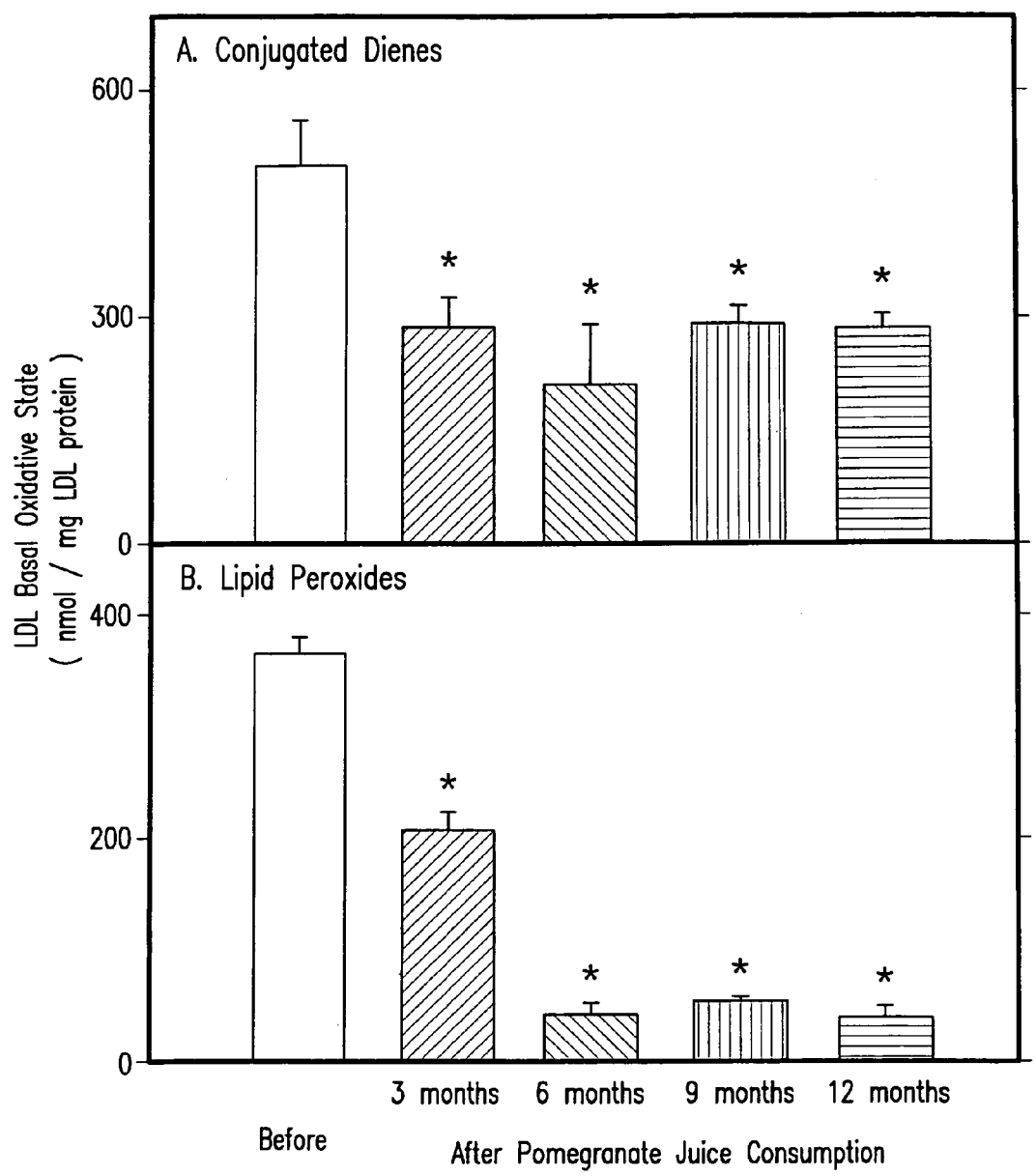
FIG. 4 shows the effect of pomegranate juice consumption by patients with carotid artery stenosis on LDL basal oxidative state.
Figure 5A:
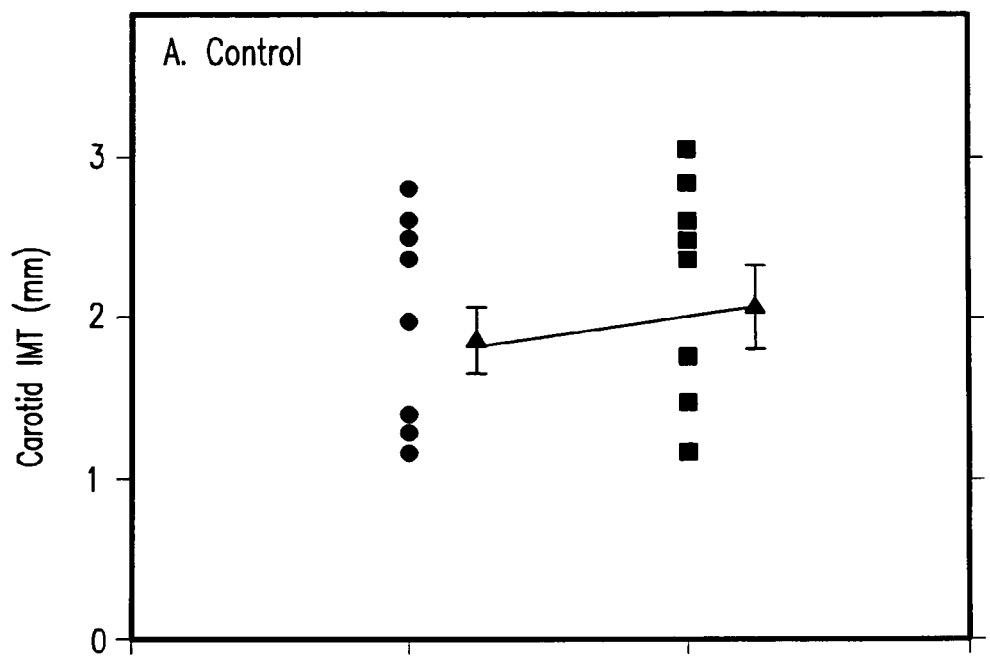
FIG. 5A shows the results of carotid intima-media thickness (IMT) in patients who did not take pomegranate juice.
Figure 5B:
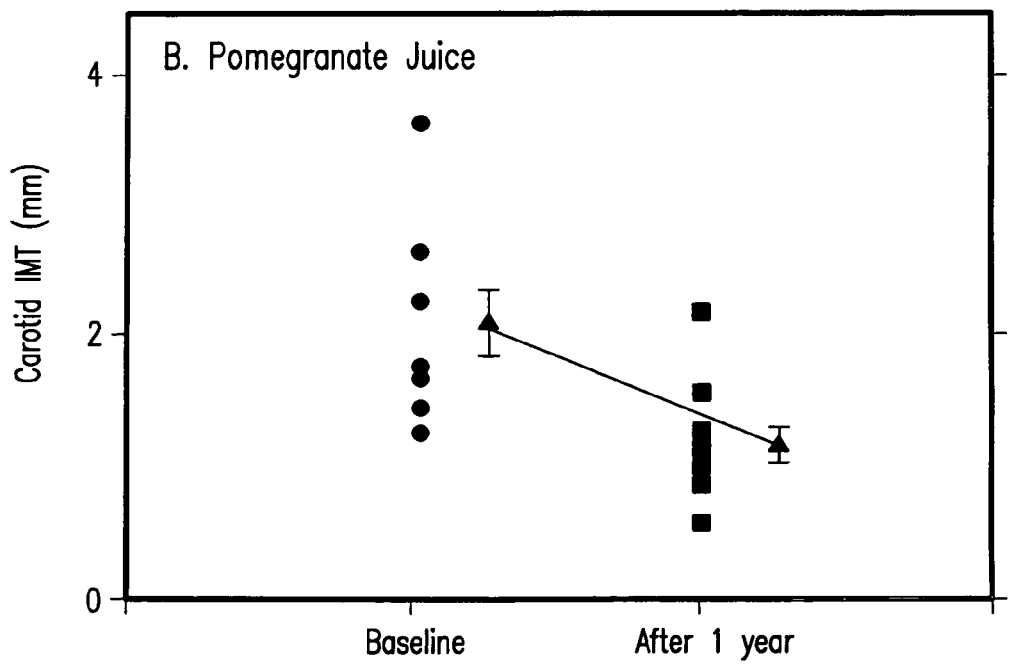
FIG. 5B shows the results of carotid IMT after pomegranate juice consumption.
Figure 5C:
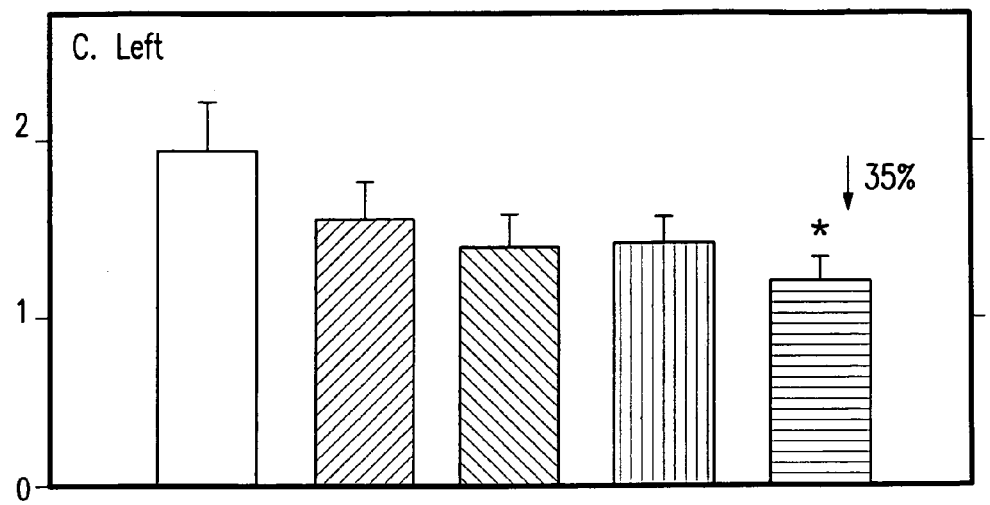
FIGS. 5C and D shows the results of IMT in the left and right artery respectively after pomegranate juice consumption.
Figure 5D:
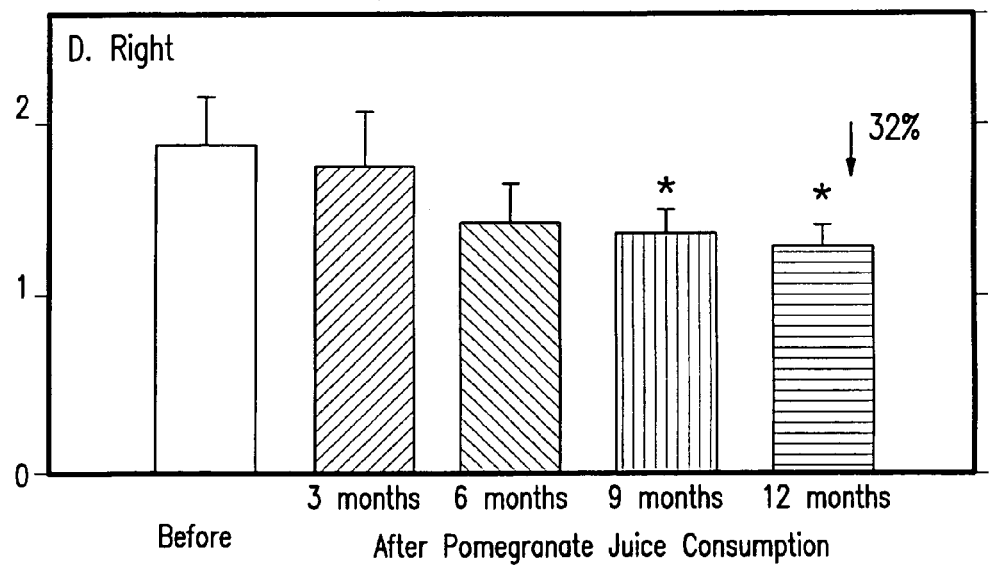

FIG. 3 shows the effect of pomegranate juice consumption by patients with carotid artery stenosis on copper ion-induced LDL oxidation. The susceptibility of LDL to copper ion-induced oxidation was gradually reduced, as observed by prolongation of the lag time required for the initiation of LDL oxidation (from 30±4 minutes before treatment to 55±5, 60±2, 64+1, and 65±2 minutes after 3, 6, 9, and 12 months of PJ consumption, respectively) (FIG. 3A). The LDL lipid peroxides content formed during copper ion-induced LDL oxidation was also reduced by 40%, 49%, 57%, and 59% after 3, 6, 9, and 12 months of PJ consumption, respectively (FIG. 3B). The results show that pomegranate juice consumption has an inhibitory effect on LDL oxidation.

FIG. 4 shows the effect of pomegranate juice consumption by patients with carotid artery stenosis on the LDL basal oxidative state. PJ consumption resulted in a significant reduction in the levels of LDL-associated lipid peroxides by 43%, 89%, 86%, and 90% after 3, 6, 9, and 12 months of PJ consumption, respectively. The results show that pomegranate juice consumption has inhibitory effect on the LDL basal oxidative state.

FIG. 5 shows the results of carotid IMT after pomegranate juice consumption. Intima-media thickness (IMT) in the more pathological carotid artery (left or right) from the control group increased significantly (p<0.01) during one year by 10% (FIG. 5A), whereas in patients that consumed PJ, a significant (p<0.01) and substantial reduction in the IMT, by 43%, was noted after one year of PJ consumption (FIG. 5B). Analysis of carotid IMT before and during PJ consumption revealed a gradual reduction of 20%, 27%, 28%, and 38% in the left carotid artery (FIG. 5C), and a reduction of 6%, 25%, 28%, and 32% in the right carotid IMT (FIG. 5D), which was observed after 3, 6, 9, and 12 months of PJ consumption, respectively, in comparison to "0 time".

Figure 6:
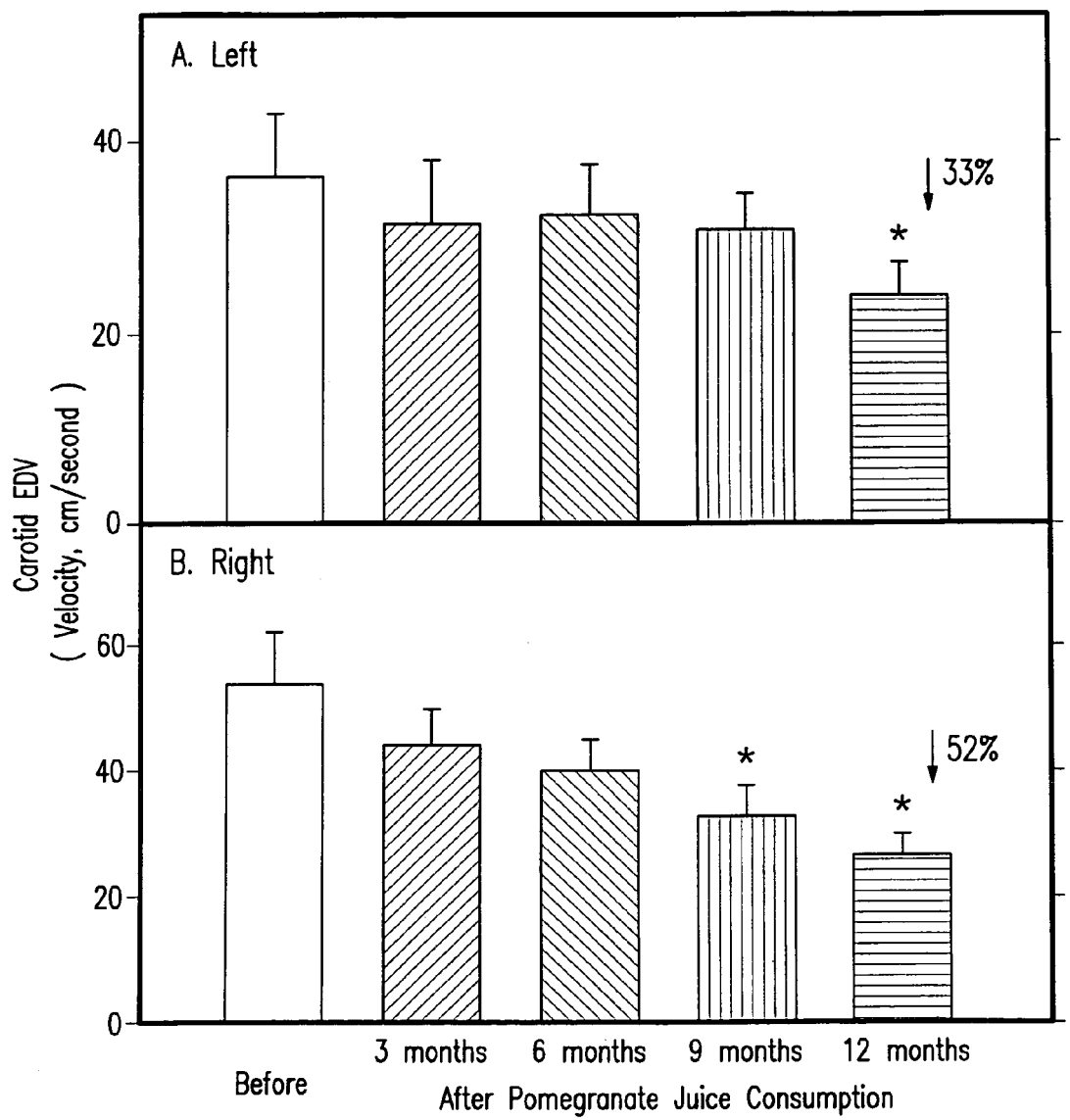
FIG. 6 shows the results of carotid end diastolic volume (EDV) after pomegranate juice consumption.

FIG. 6 shows the results of carotid end diastolic volume (EDV) after pomegranate juice consumption. The results show that pomegranate juice consumption can reduce the velocity in the left carotid artery by 11%, 14%, 17%, and by 33% (FIG. 6A), and in the right carotid artery by 20%, 26%, 40%, and 52% (FIG. 6B) after 12 months of pomegranate juice consumption. This confirms the fact that the internal diameter of the carotid artery increases after pomegranate juice consumption.

Figure 7:
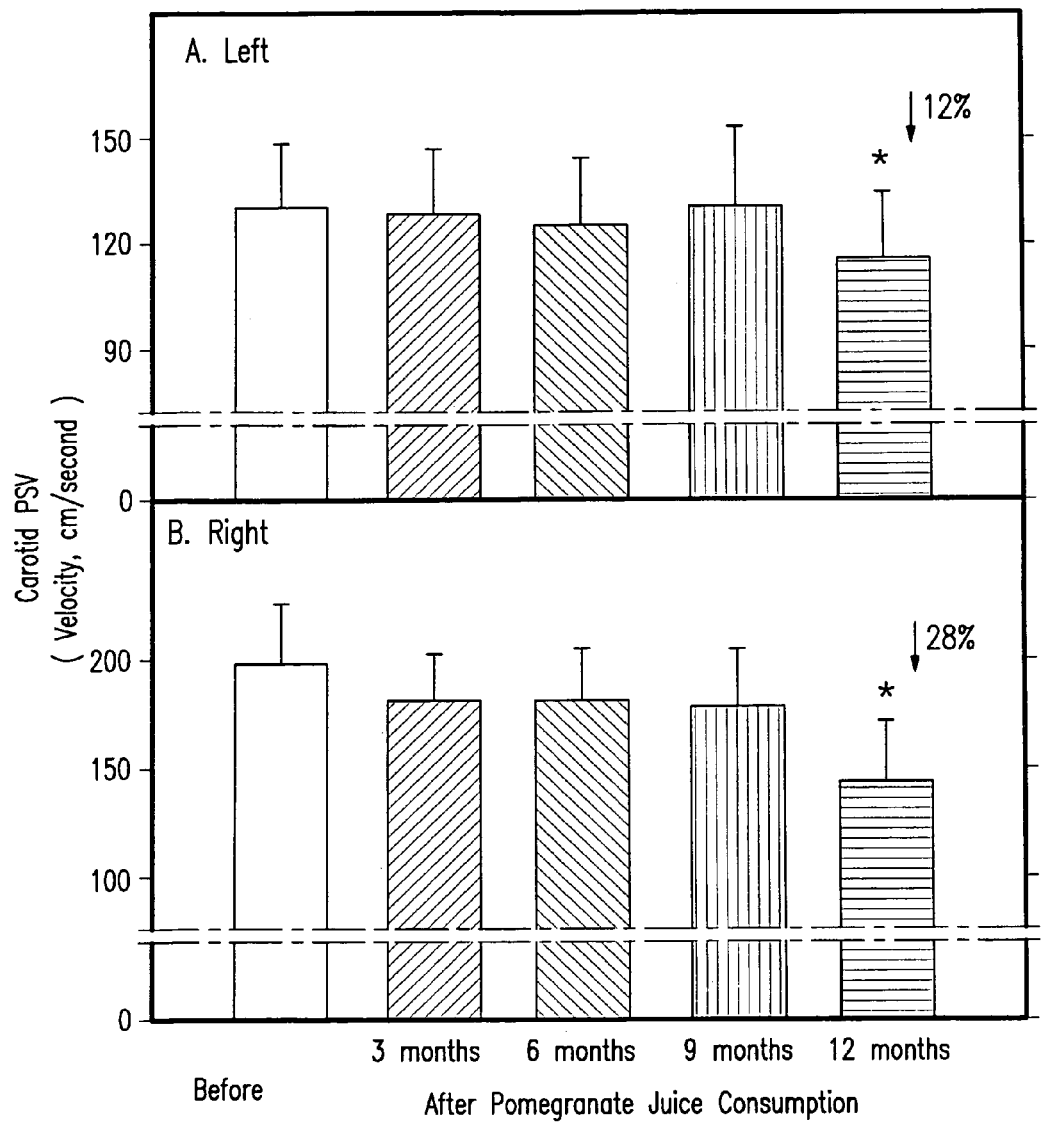
FIG. 7 shows the results of carotid peak systolic volume (PSV) after pomegranate juice consumption.

FIG. 7 shows the results of carotid peak systolic volume (PSV) after pomegranate juice consumption. The results show that pomegranate juice consumption can reduce the velocity by 12% and 28% in the left (FIG. 7A) and the right (FIG. 7B) carotid arteries, respectively, after 12 months of pomegranate juice consumption. Again, this confirms the fact that the internal diameter of the carotid artery increases after pomegranate juice consumption.

Figure 8:
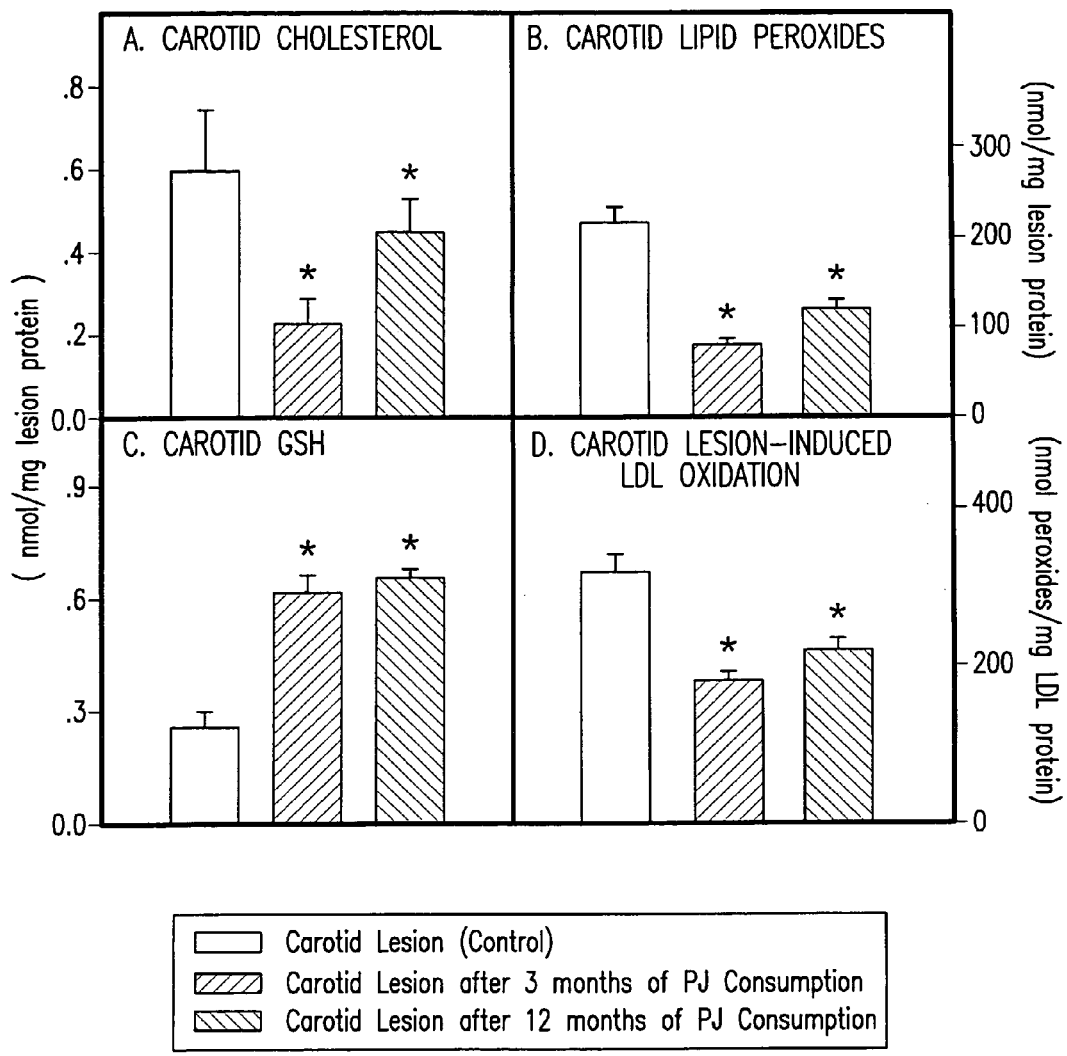
FIG. 8 shows the effect of pomegranate juice (PJ) on the carotid lesion plaque composition of patients.

FIG. 8 shows the effect of pomegranate juice (PJ) consumption by patients with carotid artery stenosis on lesion content of lipids, oxidized lipids, GSH, and on lesion-mediated oxidation of LDL. In the group of ten patients with carotid lesions who consumed PJ, one of them had to undergo carotid lesion removal at three months. Another one had to have carotid lesion removed at 12 months. The remaining patients did not need any operations. However, among the 9 patients who did not take juice extract of pomegranate, seven of the 9 patients needed to have operations to remove their carotid lesions. After the carotid lesions were obtained from the above patients, the level of cholesterol, carotid lipid peroxides, carotid GSH, and carotid lesion-included LDL oxidation in the removed carotid lesions were measured. The results are summarized in FIG. 8 as FIG. 8A to D, respectively.

The cholesterol content in the lesions was lower after PJ consumption in comparison to lesions from patients that did not consume PJ (FIG. 8A). The lipid peroxides content in lesions after PJ consumption for 3 or 12 months was significantly reduced by 61% or 44%, respectively, as compared to control lesions from untreated patients (FIG. 8B). As the balance between lesion pro-oxidants and anti-oxidants levels determines the extent of oxidized lipids, which accumulate in the lesion, we next determined the levels of reduced glutathione (GSH, the major cellular antioxidant) (43). A substantial increase in lesion GSH content, by 2.5-fold, was observed after PJ consumption (3 or 12 months, FIG. 8C). LDL oxidation by lesions derived from the patients after PJ consumption for 3 or 12 months (with no addition of copper ions), measured by the amount of lipid peroxides, was significantly (p<0.01) decreased by 43% or 32%, respectively, in comparison to LDL oxidation by lesions from untreated patients (FIG. 8D).

The results show that there is definitely a primary qualitative change in the actual lesions in people who did receive pomegranate juice. Clearly, the extract of the present invention changes the physical compositions of the plaque, and the oxidation and anti-oxidation activities within the plaque.

Discussion

The present study clearly demonstrates, for the first time, that pomegranate juice (PJ) consumption by patients with carotid artery stenosis (CAS) resulted in the following changes: a reduction in carotid IMT, a decrement in systolic blood pressure, and an inhibition in LDL oxidation. Although the use of a small number of patients could cause a statistical error, we performed power calculations using ANOVA tests and running each sample in triplicate. All the above results clearly demonstrate statistically significant anti-atherogenic effects of pomegranate juice consumption in patients with CAS.

The effect of PJ consumption on carotid lesion progression in these patients was assessed by measuring IMT, PSV, and EDV in the right and left carotid arteries before, during, and after one year of PJ consumption. A marked decrement in IMT and blood flow velocities were demonstrated after 12 months of PJ consumption, compared to values obtained at the baseline. The average IMT varies in middle aged men between 0.7 to 1.2 mm, and the progression slope of the mean maximum carotid IMT in untreated patients with carotid artery stenosis was shown to be about 0.02 mm/year (44).

In the present study, PJ consumption not only prevented the progression of the lesion, as compared to IMT in the control group, but also resulted in a reduction in the lesion size. A reduction in oxidative stress was demonstrated already after 1 month of PJ consumption, but the inhibitory effects of PJ consumption on carotid lesion parameters were demonstrated only after 9–12 months. This may indicate that if the PJ antioxidant properties are responsible for the lesion size regression, then a long period of reduced oxidative stress is required to affect carotid lesion size. In recent studies, it was demonstrated that reduced levels of antioxidants are associated with increased IMT (45), and a positive association was observed between antibodies to oxidized LDL and IMT in healthy aged men (46).

The lipid peroxidation hypothesis of atherosclerosis (2, 3, 47) is supported by the presence of oxidized lipids in atherosclerotic lesions, increased oxidative states of LDL from atherosclerotic patients (4, 48), and the anti-atherogenicity of antioxidants against LDL oxidation (4, 5). The impressive ability of PJ to inhibit LDL oxidation (basal and copper ion-induced) could be related to the high potency of PJ tannins to scavenge-free radicals (12, 13). Copper ion-induced LDL oxidation resulted in similar changes in the lipoprotein to those observed in arterial wall oxidized LDL-like particles (49, 50).

Flavonoids, as a more potent antioxidant, may overcome the limitations of vitamin E and carotenoids, and pomegranate juice as a source of one of the most potent antioxidants, such as hydrolyzable tannins and anthocyanin (12).

Serum paraoxonase (PON1) activities (arylesterase/paraoxonase) are reduced in atherosclerotic patients, such as hypercholesterolemic, diabetics, and patients with vascular diseases (51, 52). We have previously shown increased serum PON1 activity in healthy human volunteers upon PJ consumption (13). Similarly in the present study, we also showed that PJ consumption by patients with CAS resulted in a substantial increase in serum PON1 activity (up to 83% after one year). PON1, an HDL-associated esterase, protects lipoproteins from oxidation (7, 10). This protection is probably the result of paraoxonase ability to hydrolyze specific oxidized lipids in oxidized lipoproteins and in human atherosclerotic lesions (7–9). Paraoxonase is inactivated by oxidized lipids (53), and red wine flavonoids (53), as well as licorice-derived isoflavin glabridin (53), can preserve paraoxonase activity during lipoprotein oxidation. The increase in serum paraoxonase activity may be a direct effect of PJ, as we have previously demonstrated (13), or it might also be the result of the reduction in lipid peroxides, by PJ antioxidants. PJ contains very potent antioxidants and, unlike other nutrients (53), it not only preserves serum PON1, but also even increases the enzyme activity (13). Another anti-atherogenic effect of PJ consumption is its effect on blood pressure, as the patients' systolic blood pressure was significantly reduced after 12 months of PJ consumption. Similar results were recently obtained upon PJ administration to hypertensive patients (54). As reactive oxygen species contribute to endothelium-dependent contraction, antioxidants can possibly restore endothelial function, and hence, may decrease blood pressure (55, 56). The decrement in the systolic blood pressure upon PJ consumption may also be associated with reduced IMT (57).

Finally, the findings of reduced oxidative stress in lesions obtained from patients that consumed PJ, in comparison with lesions from untreated patients, could possibly be related to the effect of PJ-induced increased paraoxonase hydrolytic activity on the lesions' oxidized lipids (7–9). This phenomenon shows that, in addition to the regression of carotid lesion size, the lesion itself may be considered less atherogenic after PJ consumption, as its lipids and oxidized lipids content decreased, and since its ability to oxidize LDL was significantly reduced. Morphologically, the lesions obtained from the patients that consumed PJ were visually less fatty and fragile (data not shown), and may represent macrophage foam cells—poor carotid plaques.

It is thus concluded that, as previously shown in atherosclerotic mice (13, 58), pomegranate juice consumption by patients with carotid artery stenosis also possesses an impressive anti-atherosclerotic properties, as it substantially decreases serum oxidative stress and reduces carotid intima-media thickness.

It is an unexpected discovery of the present invention that pomegranate juice consumption can cause regression in the lesion size of carotid artery arteriosclerosis. Prior research has shown a parallel between carotid artery arteriosclerotic disease and coronary artery arteriosclerotic disease (27 to 35). Therefore, it is believed that pomegranate juice consumption would also lead to regression in coronary artery disease. In addition, due to the known relationship of the carotid and coronary artery arteriosclerotic diseases with the stroke and heart attack, it is believed that the pomegranate extract of the present invention may also be used to reduce the incidence of stroke and heart attack in a patient.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

REFERENCES (1) Griendling K K, Alexander R W. Oxidative stress and cardiovascular disease. *Circulation* 1997; 96: 3264–75.
(2) Berliner J A, Navab M, Fogelman A M, et al. Atherosclerosis: basic mechanisms, oxidation, inflammation and genetics. *Circulation* 1995; 91: 2488–96.
(3) Lusis A J. Atherosclerosis. *Nature* 2000; 407: 233–41.
(4) Aviram M. Review of human studies on oxidative damage and antioxidant protection related to cardiovascular diseases. *Free Radic Res* 2000; 33: S85–97.
(5) Aviram M, and Fuhrman B. Flavonoid antioxidants protect LDL from oxidation and attenuate atherosclerosis. *Curr Opin Lipidol* 2001; 12: 41–8.
(6) Juliano L, Mauriello A, Sbarigia E, et al. Radiolabeled native low-density lipoprotein injected into patients with carotid stenosis accumulates in macrophages of atherosclerotic plaque: Effect of vitamin E supplementation. *Circulation* 2000; 101: 1249–54.

(7) Aviram M, Rosenblat M, Bisgaier C L, et al. Paraoxonase inhibits high density lipoprotein (H DL) oxidation and preserves its functions: a possible peroxidative role for paraoxonase. *J Clin Invest* 1998; 101:1581–90.

(8) Navab M, Berliner J A, Watson A D, et al. The yin and yang of oxidation in the development of the fatty streak: a review based on the 1994 George Lyman Duff Memorial Lecture. *Arterioscler Thromb Vasc Biol* 1996; 17: 831–42.

(9) Aviram M, Hardak E, Vaya J, et al. Human serum paraoxonase (PON1), Q and R selectively decrease lipid peroxides in coronary and carotid atherosclerotic lesions: PON1 esterase and peroxidase-like activities. *Circulation* 2000; 101:2510–17.

(10) Mackness M I, Arrol S, Abott C, et al. Protection of low-density lipoprotein against oxidative modification by high-density lipoprotein associated paraoxonase. *Atherosclerosis* 1993; 104: 129–35.

(11) Langley P. Why a pomegranate?.*BMJ* 2000; 321: 1153–54.

(12) Gil M I, Tomas-Barberan F A, Hess-Pierce B, et al. Antioxidant activity of pomegranate juice and its relationship with phenolic composition and processing. *J Agric Food Chem* 2000; 10: 4581–89.

(13) Aviram M, Dornfeld L, Rosenblat M, et al. Pomegranate juice consumption reduces oxidative stress, atherogenic modifications of LDL, and platelet aggregation: studies In humans and in atherosclerotic apolipoprotein E-deficient mice. *Am J Clin Nutr* 2000; 71: 1062–76.

(14) Aviram, M. (1983) Plasma lipoprotein separation by discontinuous density gradient ultracentrifugation in hyperlipoproteinemic patients. Biochem. Med. 30, 111–118.

(15) Lowry, O. H., Rosebrough, N. J., Farr, A. L. and Randall, R. G. (1951) Protein measurement with the Folin phenol reagent. J. Biol. Chem. 193, 265–275.

(16) Buege, J. A. and Aust, S. D. Microsomal lipid peroxidation. Methods. Enzymol. 52: 302–310 (1978).

(17) Esterbauer, H., Striegl, G., Puhl, H. and Rotheneder, M. (1989) Continuous monitoring of in vitro oxidation of human low density lipoprotein. Free Radic. Res. Commun. 6, 67–75.

(18) El-Saadani, M., Esterbauer, H., El-Sayed, M., Goher, M., Nassar, A. Y., Jurgens, V. G. (1981) A spectrophotometric assay of lipid peroxides in serum lipoproteins using a commercially available reagent. J. Lipid Res. 30, 627–631.

(19) Khoo J. C., Miller E., McLoughlin P., Steinberg D. (1988) Enhanced macrophage uptake of low density lipoprotein after self-aggregation. Arteriosclerosis. 8, 348–358.

(20) Van de Lest, C. H., Versteeg, E. M., Veerkamp, J. H., van Kuppevelt, T. H. A. (1994) Spectrophotometric method for the determination of heparan sulfate. Biochim. Biophys. Acta. 1201, 305–311.

(21) Assman, G., Schriewer, H., Schmitz, G., Hagele, E. O. (1983) Quantification of high-density-lipoprotein cholesterol by preicipitation with phosphotungstic acid-MgCl$_2$. Clin. Chem. 29, 2026.

(22) Kitchen, B. J., C. J. Masters, and D. J. Winzor. (1973) Effects of lipid removal on the molecular size and kinetic properties of bovine plasma arylesterase. Biochem. J. 135 (1), 93–9.

(23) Geroulakos et al. (1994) Arterial wall changes in type 2 diabetic subjects. Diab. Med. 11, 692–695.

(24) Veller et al. (1993) Measurement of the ultrasonic intima-media complete thickness in normal subjects. J. Vasc. Surg. 17(4), 719–725.

(25) Kaplan M. et al. (2001) Pomegranate Juice Supplement to Atherosclerotic Mice Reduces Macrophage Lipid Peroxidation, Cellular Cholesterol Accumulation and Development of Atherosclerosis. J. Nutrition. 131 (8): 2082–2089.

(26) Narr Ben C., Ayed N., Metche M. Quantitative determination of the polyphenolic content of pomegranate peel. Z. Lebensm. Unters. Forsch. 203: 374–378 (1996).

(27) Mudrikova T. et al. Carotid Intima-Media Thickness in Relation to Macrovascular Disease in Patients with Bype 2 Diabetes Mellitus. Wien. Klin. Wochenschr. 112(20): 887–91.

(28) Uehara T., et al. Mr Angiographic Evaluation of Carotid and Intracranial Arteries in Japanese Patients Scheduled for Coronary Artery Bypass Grafting. Cerebrovasc. Dis. 11(4): 341–5.

(29) Lonn E., Use of Carotid Ultrasound to Stratify Risk. Can. J. Cardiol. 17 Suppl. A: 22A–5A.

(30) Ulgen M S, et al. The relationship of Coronary Artery Disease and Carotid Doppler Flow Velocity and Resistance Index In Patients with No Significant Carotid Stenosis Angiology. 52(60: 433–4.

(31) Crouse J R. Predictive Value of Carotid 2-Dimensional Ultrasound. Am J Cardiol 88(2 suppl 1): 27–30.

(32) Ropers D, et al. SAI-26 Correlation Between Calcification of the Carotid Arteries Documented by Ultrasound, Coronary Calcifications in Electron-beam Tomography, and Angiographic Coronary Artery Disease. Am J Cardiol 88 (2 Suppl):85.

(33) Denarie N. et al., Difference in Carotid Artery Wall Structure Between Swedish and French Men at Low and High Coronary Risk. Stroke 32(8): 1775–9.

(34) Vasankari T., et al., Oxidized LDL and Thickness of Carotid Intima-Media Are Associated with Coronary Atherosclerosis In Middle-aged Men: Lower Levels of oxidized LDL with Statin Therapy. Atherosclerosis 155(2): 403–12.

(35) Raitakari O T, Reduced Myocardial Flow Reserve Relates to Increased Carotid Intima-media Thickness in Healthy Young Men.

(36) Riley W A, Barnes R W, Applegate W B, et al. Reproducibility of noninvasive ultrasonic measurement of carotid atherosclerosis. *Stroke* 1992; 23: 1062–68.

(37) Bots M L, Hoes A W, Koudstaal P J, et al. Common carotid intima-media thickness and the risk of stroke and myocardial infarction: The Rotterdam Study. *Circulation* 1997; 96: 1432–37.

(38) O'Leary D H, Polak J F, Kronmal R A, et al. Carotid-artery intima and media thickness as a risk factor for myocardial infarction and stroke in older adults: Cardiovascular Health Study Collaborative Research Group. *New Engl J Med* 1999; 340: 14.22.

(39) EI-Saadani M, Esterbauer N, EI-Sayed M, et al. Spectrophotometric assay for lipid peroxides in serum lipoproteins using a commercially available reagent. *J Lipid Res* 1989; 30: 627–30.

(40) Lowry O H, Rosebrough N J, Farr L, Randall R J. Protein measurement with the Folin phenol reagent.*J Biol Chem* 1951: 193: 265–75.

(41) EI-Saadani M, Esterbauer N, EI-Sayed M, et al. Spectrophotometric assay for lipid peroxides in serum lipoproteins using a commercially available reagent. *J Lipid Res* 1989; 30: 627–30.

(42) Tietze F. Enzymatic method for quantitative determination of nanogram amounts of total and oxidized glutathione: application to mammalian blood and other tissues. *Anal Biochem* 1969; 27: 502–22.

(43) Rosenblat M, Aviram M. Macrophage glutathione content and glutathione peroxidase activity are inversely related to cell-mediated oxidation of LDL. *Free Radic Biol Med* 1998; 24: 305–17.

(44) Bots M L, Hoes A W, Koudstaal P J, et al. Common carotid intima-media thickness and the risk of stroke and myocardial infarction: The Rotterdam Study. *Circulation* 1997; 96: 1432–37.

(45) Patterson C, Madamanchi N R, Runge M S. The oxidative paradox: another piece in the puzzle. *Circ Res* 2000; 87: 1074–76.

(46) Rissanen T, Voutilainen S, Nyyssonen K, et al. Low plasma lycopene concentration is associated with increased intima-media thickness of the carotid artery wall. *Arterioscler Thromb Vasc Biol* 2000; 20: 2677–81.

(47) Hulthe J, Bokemark L, Fagerberg B. Antibodies to oxidized LDL in relation to intima-media thickness in carotid and femoral arteries in 58-year old subjectively clinically healthy men. *Arterioscler Thromb Vasc Biol* 2001; 21: 101–7.

(48) Lavy A. Brook J G, Dankner G, et al. Enhanced in vitro oxidation of plasma lipoproteins derived from hypercholesterolemic patients. *Metabolism* 1991; 40: 794–9.

(49) Esterbauer H, Rotheneder M D, Waeg G, et al. Biochemical, structural, and functional properties of oxidized low-density lipoprotein. *Chem Res Toxicol* 1990: 3: 77–92.

(50) Aviram M, Maor I, Keidar S, et al. Lesion low density lipoprotein in atherosclerotic apolipoprotein E-deficient mice and in human is oxidized and aggregated. *Biochem Biophys Res Commun* 1995; 216: 501–13.

(51) McElveen J, Mackness M I, Golley C M, et al. Distribution of paraoxon hydrolytic activity in the serum of patients after myocardial infarction. *Clin Chem* 1986; 32: 671–73.

(52) Mackness M I, Harty D, Bhatnager D, et al. Serum paraoxonase activity in familial hypercholesterolemia and insulin dependent diabetes mellitus. *Atherosclerosis* 1991; 86: 193–99.

(53) Aviram M, Rosenblat M, Billecke S, et al. Human serum paraoxonase (PON 1) is inactivated by oxidized low density lipoprotein and preserved by antioxidants. *Free Radic Biol Med* 1999; 26: 892–904.

(54) Aviram M, Dornfeld L. Pomegranate juice consumption inhibits serum angiotensin converting enzyme activity and reduces systolic blood pressure. *Atherosclerosis* 2001; 158: 195–98.

(55) Kitiyakara C, Wilcox C S. Antioxidants for hypertension. *Curr Opin Nephrol Hypertens* 1998: 7: 531–38.

(56) Lonn E M, Yusuf S, Dzavik V, et al. Effects of ramipril and vitamin E on atherosclerosis. *Circulation* 2001; 103: 919–28.

(57) Sun P, Dwyer K M, Merz C N B, et al. Blood pressure, LDL cholesterol and intima-media thickness. *Arterioscler Thromb Vasc Biol* 2000; 20: 2005–2010.

(58) Kaplan M, Hayek T, Raz A, et al. Pomegranate juice supplementation to atherosclerotic mice reduces macrophage lipid peroxidation, cellular cholesterol accumulation and development of atherosclerosis. *J Nutr* 2001; 131: 2082–2089.

(59) Abbott, C. A., Mackness, M. I., Kumar, S., Boulton, A. J. and Durrington, P. N. (1995) Serum paraoxonase activity, concentration, and phenotype distribution in diabetes mellitus and its relationship to serum lipids and lipoproteins. Arterioscler, Thromb. Vasc. Biol. 15(11), 1812–1818.

(60) Hertog, M. G. L., Feskens, E. J. M., Hollman, P. C. H., Katan, M. B., Kornhout, D. (1993) Dietary antioxidant flavonoids and risk of coronary heart disease; the Zutphen Elderly Study. Lancet. 342, 1007–1011.

(61) Maor, I., Hayek, T., Coleman, R., Aviram, M. (1997) Plasma L DL oxidation leads to its aggregation in atherosclerotic apolipoprotein E-deficient mice. Arterioscler. Thromb. Vasc. Biol. 17, 2995–3005.

What is claimed is:

1. A method of treating a person with arteriosclerosis by dispensing a solid extract prepared via a process comprising:
   (a) crushing and squeezing whole pomegranates including inner and outer peels and seeds of said whole pomegranates to yield a juice component and an insoluble by-product component;
   (b) separating said juice component from said insoluble by-product component and removing said insoluble by-product component from said juice component to produce a liquid extract from said juice component and a solid extract from said insoluble by-product component, and
   (c) administering to said person a composition comprising a therapeutically effective amount of said solid extract.

2. The method of claim 1 further comprising:
   lyophilizing said liquid extract to produce a first non-liquid extract; and, combining said first non-liquid extract with said solid extract for use in said administering.

3. The method of claim 1 further comprising:
   drying said solid extract before said administering said solid extract.

4. The method of claim 1 further comprising:
   lyophilizing said liquid extract to produce a first non-liquid extract;
   drying said solid extract to produce a second non-liquid extract; and,
   combining said first non-liquid extract with said second non-liquid extract and said solid extract into said composition.

5. The method of claim 4, wherein said solid extract comprises at least 30 to 3000 micromol of polyphenols.

6. The method of claim 4, wherein said composition further comprises a pharmaceutically acceptable carrier.

7. The method of claim 4, wherein said composition is administered orally.

8. The method of claim 4, wherein said composition is administered in a form selected from a group consisting of tablets, suspensions, implants, solutions, emulsions, capsules, powders, syrups, liquid compositions, ointments, lotions, creams, pastes, gels, and the like.

9. The method of claim 1, wherein said person is diagnosed to have carotid artery arteriosclerotic disease.

10. The method of claim 1, wherein said person has coronary artery arteriosclerotic disease.

11. A method of treating a person with an increased intima-media thickness of an artery, by dispensing a solid extract prepared via a process comprising:
    (a) crushing and squeezing whole pomegranates to yield a juice component and an insoluble by-product component;
    (b) separating said juice component from said insoluble by-product component and removing said insoluble by-product component from said juice component to produce liquid extract from said juice component and a solid extract from said insoluble by-product component; and, (c) administering to said person a composition comprising an amount of said solid extract which is therapeutically effective to reduce the intima-media thickness of said artery.

12. The method of claim 11 further comprising:
lyophilizing said liquid extract to produce a first non-liquid extract; and,
combining said first non-liquid extract with said solid extract for use in said administering.

13. The method of claim 12 further comprising:
drying said solid extract before said administering said solid extract.

14. The method of claim 11 further comprising:
lyophilizing said liquid extract to produce a first non-liquid extract;
drying said solid extract to produce a second non-liquid extract; and,
combining said first non-liquid extract with said second non-liquid extract and said solid extract into said composition.

15. The method of claim 11 wherein said person is diagnosed as having risk factors associated with arteriosclerotic disease.

16. The method of claim 11, wherein said person has risk factors associated with coronary artery arteriosclerotic disease.

17. The method of claim 11, wherein said person has risk factors associated with carotid artery stenosis.

18. The method of claim 11, wherein the said solid extract contains at least 30 to 3000 micromol of polyphenols.

* * * * *